(12) United States Patent
Quinn et al.

(10) Patent No.: US 7,404,329 B2
(45) Date of Patent: Jul. 29, 2008

(54) PRESSURE GAUGE FOR USE WITH AN AIRWAY LUMEN

(75) Inventors: Brad Quinn, Indianapolis, IN (US); George V McGarrity, Indianapolis, IN (US)

(73) Assignee: Engineered Medical Systems, Inc., Indianapolis, IN (US)

( * ) Notice: Subject to any disclaimer, the term of this patent is extended or adjusted under 35 U.S.C. 154(b) by 497 days.

(21) Appl. No.: 10/904,991

(22) Filed: Dec. 8, 2004

(65) Prior Publication Data

US 2006/0118123 A1 Jun. 8, 2006

(51) Int. Cl.
*G01L 7/08* (2006.01)
(52) U.S. Cl. ..................... 73/716; 128/207.15; 73/715
(58) Field of Classification Search ............ 73/700–756
See application file for complete search history.

(56) References Cited

U.S. PATENT DOCUMENTS

| | | | |
|---|---|---|---|
| 4,016,885 A | 4/1977 | Bruner | |
| 4,471,778 A | 9/1984 | Toye | |
| 4,617,015 A | 10/1986 | Foltz | |
| 4,898,168 A * | 2/1990 | Yule | ............... 128/207.15 |
| 4,926,885 A | 5/1990 | Hinkle | |
| 5,218,970 A * | 6/1993 | Turnbull et al. | ............ 600/561 |
| 5,235,973 A | 8/1993 | Levinson | |
| 5,487,383 A | 1/1996 | Levinson | |
| 5,557,049 A * | 9/1996 | Ratner | ......................... 73/715 |
| 5,873,362 A | 2/1999 | Parker | |
| 6,386,199 B1 | 5/2002 | Alfery | |
| 6,530,898 B1 | 3/2003 | Nimkar | |
| 6,553,993 B2 * | 4/2003 | Toti et al. | ............... 128/207.14 |
| 2002/0157665 A1 | 10/2002 | Igarashi | |

* cited by examiner

*Primary Examiner*—Andre S. Allen
*Assistant Examiner*—Jermaine Jenkins
(74) *Attorney, Agent, or Firm*—Swanson & Bratschun, LLC

(57) ABSTRACT

A pressure gauge for use in combination with an airway lumen having an inflatable cuff, the pressure gauge including a housing and a flexible diaphragm within the housing defining a fluid tight chamber with the chamber in fluid communication with the cuff. In use a surface of the diaphragm moves along an axis in response to a fluid pressure change in the cuff. The pressure gauge also includes a radial indicator attached to the housing extending transverse the surface of the diaphragm and a linear to radial linkage operatively associated between the surface of the diaphragm and the radial indicator to cause radial movement of the indicator. In one embodiment the linear to radial linkage includes a gear tooth rack associated with the surface of the diaphragm and a pinion gear mating with the rack. In such an embodiment the radial indicator may further include a pointer operatively associated with the pinion gear. This embodiment will also include a scale having select markings which in conjunction with the pointer allow a user to read the fluid pressure within the cuff.

17 Claims, 3 Drawing Sheets

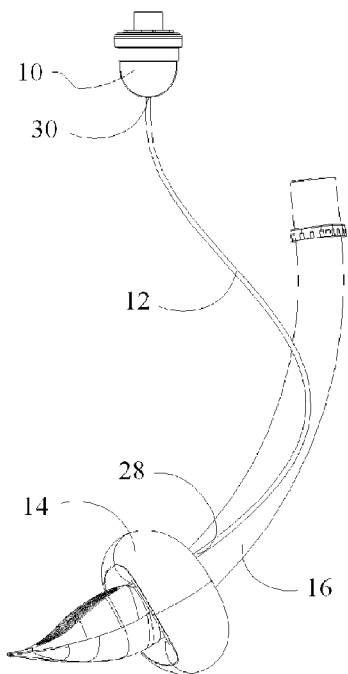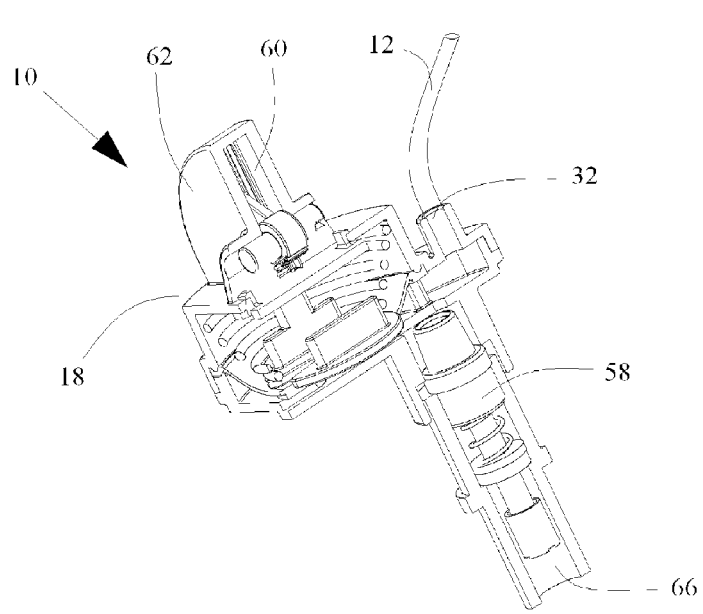
Fig. 1                    Fig. 2

PRESSURE GAUGE FOR USE WITH AN AIRWAY LUMEN

TECHNICAL FIELD

The present invention is directed towards pressure gauges, and more particularly toward a pressure gauge for use in combination with an airway lumen having an inflatable cuff.

BACKGROUND ART

Various types of medical devices have been developed to provide medical access to a human airway. Representative devices include endotracheal tubes used in emergency or other situations to prevent blockage of a patient's airway and/or to provide general anesthesia to the patient's lungs during a surgical procedure. A typical endotracheal tube includes a flexible lumen which is inserted orally such that in use the distal end of the lumen is located within the patient's trachea. A representative endotracheal tube is shown in Parker, U.S. Pat. No. 5,873,362.

Another type of device which can be used to access a human airway is a tracheostomy tube, also known as a tracheotomy tube. These devices are inserted in an emergency procedure directly into the trachea from outside a patient's body. Tracheostomy devices also include a relatively less flexible lumen.

A representative third class of devices are oral airways positioned with a distal end in a patient's hypopharynx adjacent to the glottis. Representative is a perilaryngeal airway shown in Alfrey, U.S. Pat. No. 6,386,199.

Endotracheal tubes, tracheostomy tubes, oral airways, and similar apparatus are referred to collectively herein as "airway lumens." A common feature of many types of airway lumens is an inflatable cuff associated with the distal portion of the lumen body.

Typically, an airway lumen is inserted into the mouth and deep into the patient's throat (e.g., hypopharynx or trachea) with the cuff near the leading distal end. The cuff, once inflated, seals the patient's airway between the lumen and the surrounding tissue. In order to effectively use an airway lumen, the cuff must be inflated to an appropriate pressure. However, since the cuff is seated deep in the patient's throat, visual observation of proper inflation is not possible. Over inflation of a cuff can cause tissue damage such as tracheal necrosis and/or stenosis. On the contrary, under inflation of the cuff will not properly seal the patient's airway, thus limiting the effectiveness of the airway lumen and potentially allowing harmful fluids to reach the patient's lungs.

In many known airway lumen devices, the inflatable cuff is connected in fluid communication with a small balloon commonly called a pilot cuff which is positioned outside of the patient's body. As the inflatable cuff is inflated within the patient's body, the pilot cuff is simultaneously inflated on the exterior of the patient's body. Thus, a pilot cuff provides a medical technician with a visual and tactile indicator of the fluid pressure within the inflatable cuff. The proper use of a pilot cuff requires a great deal of technical experience and can be quite imprecise, particularly if used in an emergency situation.

Accordingly, several varieties of pressure sensing devices have been developed which provide a more or less precise indication of the fluid pressure within an inflatable cuff. Certain devices, such as that taught by Levinson, U.S. Pat. No. 5,487,383, feature sophisticated computerized monitoring and control of cuff fluid pressure. This type of device is most suitable for use in a hospital setting, and is a relatively expensive solution to the problem of achieving proper cuff inflation.

Foltz, U.S. Pat. No. 4,617,015; Bruner, U.S. Pat. No. 4,016,885; and Igarashi, US 2002/0157665A1 each disclose more simplified mechanical pressure gauges which feature an indicator and scale to represent the fluid pressure within an inflatable cuff. These gauges are more mobile and thus more suitable for emergency use than a sophisticated computer operated apparatus. The Foltz, Bruner and Igarashi gauges, however, require that cuff pressure be read from a lined scale, which could result in interpretation errors in an emergency setting. In addition, mechanical gauges such as those taught by Foltz, Bruner, or Igarashi do not directly indicate an acceptable range of "in use" pressures within the inflatable cuff which are readable with a quick glance.

The present invention is directed toward overcoming one or more of the problems discussed above.

SUMMARY OF THE INVENTION

A pressure gauge for use in combination with an airway lumen having an inflatable cuff, includes a housing and a flexible diaphragm within the housing defining a fluid tight chamber with the chamber in fluid communication with the cuff. In use a surface of the diaphragm moves along an axis in response to a fluid pressure change in the cuff. The pressure gauge also includes a radial indicator attached to the housing extending transverse the surface of the diaphragm and a linear to radial linkage operatively associated between the surface of the diaphragm and the radial indicator. The linear to radial linkage is configured to cause radial movement of the indicator in response to axial movement of the surface of the diaphragm.

The pressure gauge may further include a tube providing for the fluid communication between the inflatable cuff and the pressure gauge and a biasing mechanism operatively associated with the surface of the diaphragm. The biasing mechanism may be a spring.

In one embodiment the linear to radial linkage includes a gear tooth rack associated with the surface of the diaphragm and a pinion gear mating with the rack. In such an embodiment the radial indicator may further include a pointer operatively associated with the pinion gear.

A further embodiment may include a scale having select markings which in conjunction with the pointer allow a user to read the fluid pressure within the cuff. Preferably, the select markings of the scale graphically define more than one zone with at least one zone corresponding to an acceptable in use fluid pressure within the inflatable cuff. The zones of acceptable or unacceptable fluid pressure may be defined by distinct colors. The zone corresponding to an acceptable inflation pressure may correspond to a fluid pressure within the cuff substantially within the range of 25 cm Hg to 35 cm Hg. The pressure gauge may also include a relief valve in fluid communication with the airtight chamber.

Although described above with respect to a pressure gauge, the present invention may be implemented as a scale for use with a pressure gauge in fluid communication with an inflatable cuff, or as an airway lumen including a lumen body, an inflatable cuff and a pressure gauge as described above.

BRIEF DESCRIPTION OF THE DRAWINGS

FIG. 1 is a perspective view of an airway lumen with an inflatable cuff associated with a pressure gauge consistent with the present invention;

FIG. 2 is a perspective view of the exterior housing of a pressure gauge consistent with the present invention;

DETAILED DESCRIPTION OF THE PREFERRED EMBODIMENT

A pressure gauge 10 is shown in FIG. 1 connected in fluid communication through a tube 12 to an inflatable cuff 14 associated with an airway lumen 16. The airway lumen 16 illustrated in FIG. 1 is a supraglottic airway, however, the present invention is applicable to any type of airway lumen which features an inflatable cuff 14. Other types of airway lumen not shown in FIG. 1 include endotracheal tubes, tracheostomy and tracheotomy tubes, and similar devices which have a lumen and provide medical access to the human airway.

Figure 3:
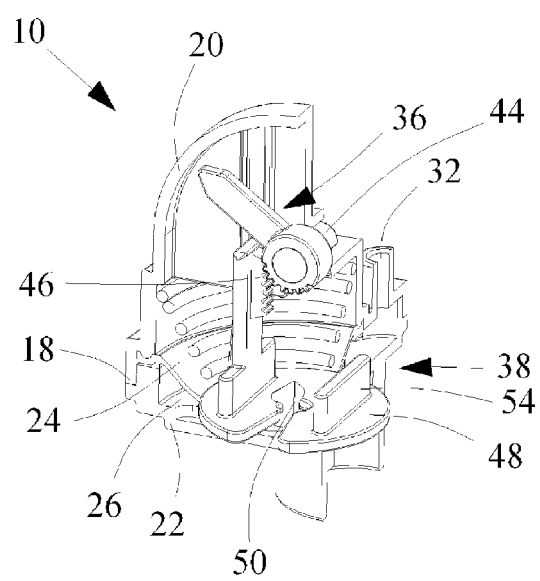
FIG. 3 is a cutaway perspective view of a pressure gauge consistent with the present invention.
Figure 4:
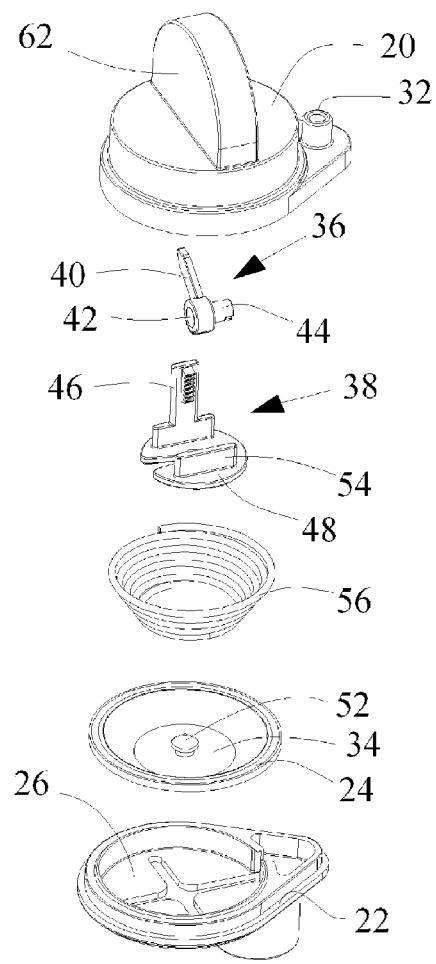
FIG. 4 is an exploded perspective view of a pressure gauge consistent with the present invention.

As shown in FIG. 2, FIG. 3, and FIG. 4, the pressure gauge 10 includes a housing 18. The housing 18 may include an upper portion 20 and a lower portion 22 which are bonded together to define an interior space. The upper portion 20 and lower portion 22 of the housing 18 are best shown in the exploded view of FIG. 4.

A flexible diaphragm 24 is received in the housing 18 and defines a fluid tight chamber 26 within the housing 18. The chamber 26 is in fluid communication with the inflatable cuff 14 associated with the airway lumen 16. As shown in FIG. 1, the chamber 26 will typically be maintained in fluid communication with the inflatable cuff 14 via the tube 12. The tube 12 has a distal end 28 opening into the inflatable cuff 14, and a proximal end 30 opening into the chamber 26. Typically, the proximal end 30 of the tube 12 will be engaged with an intake port 32 associated with the housing 18.

The diaphragm 24 will include a surface 34 opposite the fluid tight chamber 26. Both the shape of the diaphragm 24 and the selection of a flexible but fluid tight material for the construction of the diaphragm 24 allow the surface 34 to move in a linear manner along an axis normal to the surface 34 in response to a fluid pressure change within the chamber 26 corresponding to a fluid pressure change in the cuff 14. An exemplary diaphragm material is silicone rubber.

The housing 18 is also operatively associated with a radial indicator 36 extending transverse the surface 34 of the diaphragm 24. In addition, a linear-to-radial linkage 38 is operatively associated between the surface 34 of the diaphragm 24 and the radial indicator 36. The linear to radial linkage 38 is configured to cause radial movement of the radial indicator 36 in response to axial movement of the surface 34 of the diaphragm 24.

Figure 5:
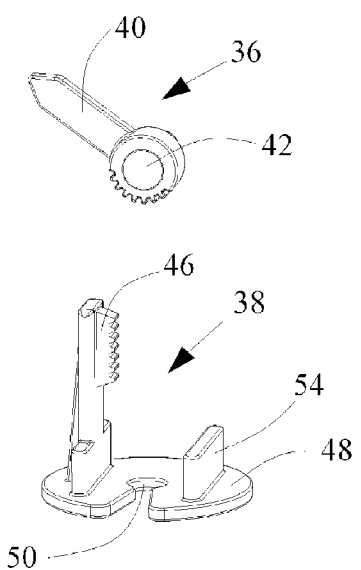
FIG. 5 is an exploded perspective view showing detail of a linear to radial linkage and a radial indicator consistent with the present invention.

As shown in FIG. 3, FIG. 4, and FIG. 5, an exemplary radial indicator 36 includes a pointer 40 attached to a pinion gear 42 associated with an axle 44. The axle 44 is received in the housing 18 as shown in FIG. 3 such that the radial indicator 36 and pointer 40 may move radially in a plane transverse to the surface 34 of the diaphragm 24.

In the exemplary embodiment, the radial indicator 36 is actuated by a linear-to-radial linkage 38 which includes a toothed rack 46 which extends along the axis of diaphragm movement, and which is configured to mate with the pinion gear 42. The toothed rack 46 may be mounted on a platform 48 which defines an opening 50 which may be clipped onto an attachment structure such as button 52 formed on the surface 34 of the diaphragm 24. In addition, the linear-to-radial linkage 38 may include a counterweight structure 54 placed opposite the toothed rack 46 on the platform 48 to provide for balanced forces against the diaphragm 24 and assure that the linear-to-radial linkage 38 moves in a linear fashion in response to fluid pressure changes communicated to the diaphragm 24.

Preferably, a biasing mechanism 56 will be operatively associated with the diaphragm 24 to bias the diaphragm 24 towards the chamber 26 and to determine the calibration and sensitivity of the pressure gauge 10. An exemplary spring basing mechanism 56 is illustrated in FIG. 3 and FIG. 4. In addition, a bleed valve 58 as shown in FIG. 2 may be operatively associated with the fluid tight chamber 26 to provide for the simple reduction of the fluid pressure within the chamber 26 and inflatable cuff 14 as needed.

Figure 6:
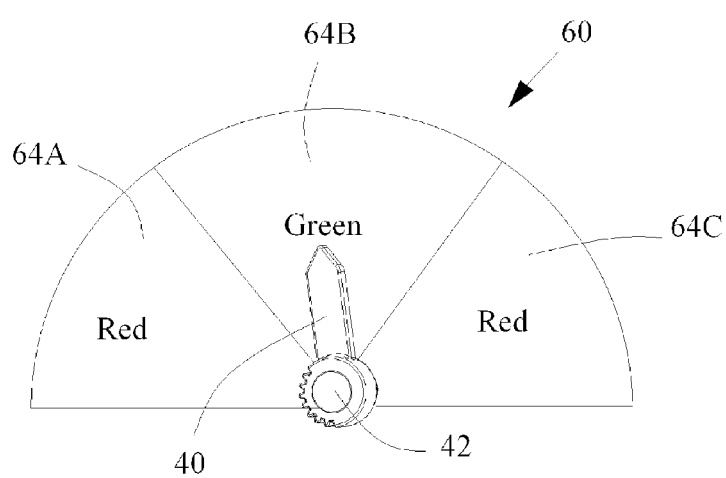
FIG. 6 is a plan view of a scale consistent with the present invention.

One embodiment of the pressure gauge 10 will further include a scale 60 disposed within the housing 18 and operatively associated with the radial indicator 36. As shown in FIG. 6, the scale 60 may be a semicircular, planar surface positioned behind the pointer 40. The embodiment of the pressure gauge 10 illustrated in FIGS. 2-4 features a housing 18 which has a semicircular viewing structure 62 molded into the upper portion 20. In this embodiment the semicircular viewing structure 62 is fabricated from a transparent or semi-transparent material and the scale 60 is affixed to a side of the semicircular viewing structure 62. Exemplary materials from which a transparent or semi-transparent viewing structure 62 may be fabricated include, but are not limited to, (poly)styrene, polycarbonate or K-resin. An enclosed transparent semicircular viewing structure as shown in FIG. 2 is advantageous for a medical device since the scale 60 and pointer 40 are fully enclosed and thus my be easily sterilized and protected from body fluids. However, other configurations of a pointer 40 and scale 60 are within the scope of the present invention.

The scale 60 will have select markings which, in conjunction with the pointer 40, allow a user to read the fluid pressure within the chamber 26 and cuff 14. As shown in FIG. 6, the select markings are preferably a simple graphic which defines more than one zone, with at least one zone corresponding to an acceptable "in use" fluid pressure within the inflatable cuff 14. For example, the scale 60 of FIG. 6 shows three zones 64A, 64B, 64C, with each zone being identified by a distinct color. In the FIG. 6 embodiment zone 64A indicates under-inflation and zone 64C indicates over-inflation. These zones may be colored red for example. On the contrary, zone 64B indicates the proper "in use" inflation pressure for the inflatable cuff 14, and may be colored a contrasting green for example. Thus, as is discussed in detail below, the appropriate inflation pressure for an inflatable cuff 14 may be accurately and quickly determined even under emergency conditions. Although the scale shown in FIG. 6 employs separate color coded zones to identify both acceptable and unacceptable inflation pressures, other methods of graphically indicating acceptable and unacceptable pressure zones are within the scope of the present invention.

Preferably the zone which corresponds to an acceptable "in use" pressure within the inflatable cuff (zone 60B) corresponds to a fluid pressure essentially within the range of 25 cm Hg minimum fluid pressure to 35 cm Hg maximum fluid pressure. The above range is generally medically accepted as the most suitable range for sealing a typical inflatable cuff to the tracheal wall, without risk of tissue damage resulting from over inflation.

In use, a physician, nurse or emergency medical technician will intubate a patient with an appropriate airway lumen 16 having an inflatable cuff 14 in fluid communication with a pressure gauge 10. The medical technician will take care that the inflatable cuff 14 is properly positioned in the patient's airway. Upon placement of the airway lumen 16, the inflatable cuff 14 may be inflated in a conventional manner. Typically the inflatable cuff 14 is inflated by forcing air into the cuff from an inflation syringe associated with the proximal end 30 of the tube 12. Although not shown on FIG. 2, the inflation syringe may be engaged with the opening 66 of the bleed valve 58 opposite the fluid tight chamber 26.

As the inflation syringe is actuated or air is otherwise applied to the inflatable cuff 14, the medical technician may observe the movement of the pointer 40 with respect to the scale 60. As the cuff 14 fully inflates and begins to pressurize, the fluid pressure within the cuff 14 will be communicated via the tube 12 to the fluid tight chamber 26 and will flex the diaphragm 24. The diaphragm 24, due to the nature of its construction and configuration, will cause linear motion of the surface 34 along an axis normal to the surface 34 and away from the chamber 26. This motion of the diaphragm 24 will be translated to the linear to radial linkage 38, and subsequently to the radial indicator 36. If the embodiment of the radial indicator 36 includes a pinion gear 42 and pointer 40 as shown in FIGS. 3-6, increased pressure within the inflatable cuff 14 will result in movement of the pointer 40 from a rest position, through zone 64A and subsequently into zone 64B. When the medical technician observes that the pointer 40 has reached or become centered in zone 64B, the technician may cease applying air to the cuff 14 from the inflation syringe or other air source. If the pointer passes through zone 64B into zone 64C the medical technician may determine at a glance that over inflation has occurred and may bleed an appropriate amount of air out of the system through the bleed valve 58.

The embodiment of the pressure gauge 10 shown in FIGS. 1-4 features a pointer 40 which moves radially within a plane which is transverse to the surface 34 of the diaphragm 24. This configuration causes the pointer 40 and scale 60 to lie parallel with the tube 12. Accordingly, the pointer 40 and scale 60 are positioned for viewing at a glance by a medical technician whose hands are occupied with the intubation and inflation steps in an emergency setting.

Preferably the configuration and material chosen for the diaphragm 24, the spring selected for the biasing member 56, the mechanics of the linear to radial linkage 38 and the mechanics of the radial indicator 36 are selected so that the pointer 40 points to zone 62B at inflation pressures between 25 cm Hg and 35 cm Hg, thus allowing a medical technician to rapidly and accurately determine the generally accepted medically correct inflation pressure for an inflatable cuff 14 associated with an airway lumen 16.

The foregoing description of the present invention has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiment described and shown in the figures was chosen and described in order to best explain the principles of the invention, the practical application, and to enable others of ordinary skill in the art to understand the invention for various embodiments with various modifications as are suited to the particular use contemplated.

What is claimed is:

1. A pressure gage for use in combination with an airway lumen having an inflatable cuff, the pressure gage comprising: a housing; a flexible diaphragm received in the housing defining a fluid tight chamber within the housing, the chamber being in fluid communication with the cuff, the chamber further not being in fluid communication with an airway defined by the airway lumen whereby a surface of the diaphragm moves along an axis in response to a fluid pressure change in the cuff; a radial indicator attached to the housing extending transverse the surface of the diaphragm; and a linear to radial linkage operatively associated between the surface of the diaphragm and the radial indicator to cause radial movement of the indicator in response to axial movement of the surface of the diaphragm.

2. The pressure gage of claim 1 further comprising a tube providing for the fluid communication between the inflatable cuff and the pressure gage, the tube having a distal end opening into the cuff and a proximal end opening into the pressure gage.

3. The pressure gage of claim 1 further comprising a biasing mechanism operatively associated with the surface of the diaphragm.

4. The pressure gage of claim 3 wherein the biasing mechanism is a spring.

5. The pressure gage of claim 1 wherein the linear to radial linkage comprises: a gear toothed rack operatively associated with the surface of the diaphragm; and a pinion gear mating with the rack.

6. The pressure gage of claim 5 wherein the radial indicator is a pointer operatively associated with the pinion gear.

7. The pressure gage of claim 1 wherein the radial indicator is a pointer.

8. The pressure gage of claim 7 further comprising a scale operatively associated with the pointer, the scale having select markings which, in conjunction with the pointer allow a user to read the fluid pressure within the cuff.

9. The pressure gage of claim 8 wherein the select markings graphically define more than one zone with at least one zone corresponding to an acceptable in-use fluid pressure within the inflatable cuff.

10. The pressure gage of claim 9 wherein the more than one zone is identified on the scale by distinct colors.

11. The pressure gage of claim 9 wherein at least one of the zones corresponding to an acceptable in-use pressure within the inflatable cuff corresponds to a fluid pressure within the cuff substantially within the range of 25 cm Hg to 35 cm Hg.

12. The pressure gage of claim 1 further comprising a relief valve in fluid communication with the chamber.

13. An airway lumen comprising: a lumen body suitable for placement in fluid communication with a human airway; an inflatable cuff associated with the lumen body; a pressure gage in fluid communication with the inflatable cuff and not in fluid communication with the human airway, the pressure gage further comprising; a housing; a flexible diaphragm received in the housing defining a fluid tight chamber within the housing, the chamber being in fluid communication with the cuff, whereby a surface of the diaphragm moves along an axis in response to a fluid pressure change in the cuff; a radial indicator attached to the housing extending transverse the surface of the diaphragm; and a linear to radial linkage operatively associated between the surface of the diaphragm and the radial indicator to cause radial movement of the indicator in response to axial movement of the surface of the diaphragm.

14. The airway lumen of claim 13 wherein the linear to radial linkage comprises: a gear toothed rack operatively associated with the surface of the diaphragm; and a pinion gear mating with the rack.

15. The airway lumen of claim 13 wherein the radial indicator is a pointer operatively associated with the pinion gear.

16. The airway lumen of claim 15 further comprising a scale operatively associated with the pointer, the scale having select markings which, in conjunction with the pointer allow a user to determine the fluid pressure within the cuff.

17. The airway lumen of claim 16 wherein the select markings graphically define more than one zone with at least one zone corresponding to an acceptable in-use fluid pressure within the inflatable cuff.

* * * * *